US00PP36455P2

(12) United States Plant Patent
Hermans

(10) Patent No.: US PP36,455 P2
(45) Date of Patent: Feb. 18, 2025

(54) ***TAXUS* PLANT NAMED 'HER2016T02'**

(50) Latin Name: *Taxus baccata*
Varietal Denomination: HER2016T02

(71) Applicant: Herplant BVBA, Beerse (BE)

(72) Inventor: Didier Hermans, Beerse (BE)

(73) Assignee: HERPLANT BVBA, Beerse (BE)

( * ) Notice: Subject to any disclaimer, the term of this patent is extended or adjusted under 35 U.S.C. 154(b) by 0 days.

(21) Appl. No.: 18/412,548

(22) Filed: Jan. 14, 2024

(51) Int. Cl.
*A01H 7/00* (2006.01)

(52) U.S. Cl.
USPC ..... Plt./215
CPC ..... *A01H 7/00* (2013.01)

(58) Field of Classification Search
USPC ..... Plt./215
CPC ..... A01H 7/00
See application file for complete search history.

(56) References Cited

PUBLICATIONS https://floranews-com.translate.goog/nieuws/18967/Gemoedelijke_sfeer_op_GrootGroenPlus_2022_en%23128248.html?_x_tr_sl=nl&_x_tr_tl=en&_x_tr_hl=en&_x_tr_pto=sc; Jun. 10, 2022; 7 pages.*
https://szkolkarstwo-pl.translate.goog/szkolkarstwo/nowe-odmiany-na-targach-grootgroenplus-2022/?_x_tr_sl=pl&_x_tr_tl=en&_x_tr_hl=en&_x_tr_pto=sc; Oct. 14, 2022; 7 pages.*
https://www-boom--in--business-nl.translate.goog/article/40550/noviteiten-2022?_x_tr_sl=nl&_x_tr_tl=en&_x_tr_hl=en&_x_tr_pto=sc; Sep. 19, 2022; 5 pages.*
In re Wingen; Feb. 2, 2023; 9 pages.*

* cited by examiner

*Primary Examiner* — Kent L Bell
(74) *Attorney, Agent, or Firm* — Penny J. Aguirre

(57) ABSTRACT

A new cultivar of *Taxus* plant named 'HER2016T02' that is characterized by its refined, small leaves, its compact and very dense plant habit with short internodes, its healthy, dark green foliage, and its fast-rooting habit.

2 Drawing Sheets

Botanical classification: *Taxus baccata.*
Variety denomination: 'HER2016T02'.

CROSS REFERENCE TO A RELATED APPLICATION

This application is related to a European plant breeders' rights application filed on Jan. 24, 2022, application No. 2022/0226. The Applicant received the information for the Plant breeders' rights application directly from the Inventor.

BACKGROUND OF THE INVENTION

The present invention relates to a new and distinct cultivar of *Taxus baccata* and will be referred to hereafter by its cultivar name, 'HER2016T02'. 'HER2016T02' is a new cultivar of yew grown for use as an ornamental landscape plant with suitability for landscapes and containers.

The new cultivar was developed from an ongoing breeding program by the Inventor at his nursery in Beerse, Belgium. The goal of the breeding program was to select a new cultivar of *Taxus baccata* that has a compact plant habit, short leaf internodes, healthy green foliage, and a good rooting habit. 'HER2016T02' arose from open pollination of unnamed, unpatented seedlings from the Inventor breeding program. All seeds collected from the open-pollination were pooled and therefore the parents plants are unknown. The Inventor selected the new cultivar as a single unique plant from amongst the resulting seedlings in 2016.

Asexual propagation of the new cultivar was first accomplished by the Inventor by stem cuttings in 2016 in Beerse, Belgium. Asexual propagation of the new cultivar by stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'HER2016T02' as a unique cultivar of *Taxus*.

1. 'HER2016T02' exhibits refined, small leaves.
2. 'HER2016T02' exhibits a compact and very dense plant habit with short internodes.
3. 'HER2016T02' exhibits healthy, dark green foliage.
4. 'HER2016T02' exhibits fast-rooting habit.

'HER2016T02' can be most closely compared to typical plants of *Taxus baccata, Taxus* x *media* cultivar 'HER2009T01' (not patented), and *Taxus baccata* 'Her2009T03' (not patented). Typical plants of the species *Taxus baccata* differ from 'HER2016T02' in having longer and broader leaves, a less compact plant size, longer internodes, less branching, and a slower rate of rooting. 'HER2009T01' differs from 'HER2016T02' in having longer and broader leaves, a less compact plant size, and longer internodes, 'Her2009T03' differs from 'HER2016T02' in having variegated foliage; green centers and light green to white margins.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include website listings by GrootGroenPlus (facebook) as a notice that the claimed plant was registered for a new variety show, Plantipp (the breeders representative for licensing propagators), and Visions Pictures.

BRIEF DESCRIPTION OF THE DRAWINGS

The accompanying color photographs illustrate the overall appearance and distinct characteristics of the new *Taxus*. The photographs were taken of plants 4 years in age as grown outdoors in 19-cm container in Beerse, Belgium.

The photograph in FIG. 1 provides a side view of the plant habit of 'HER2016T02'.

Figure 1:
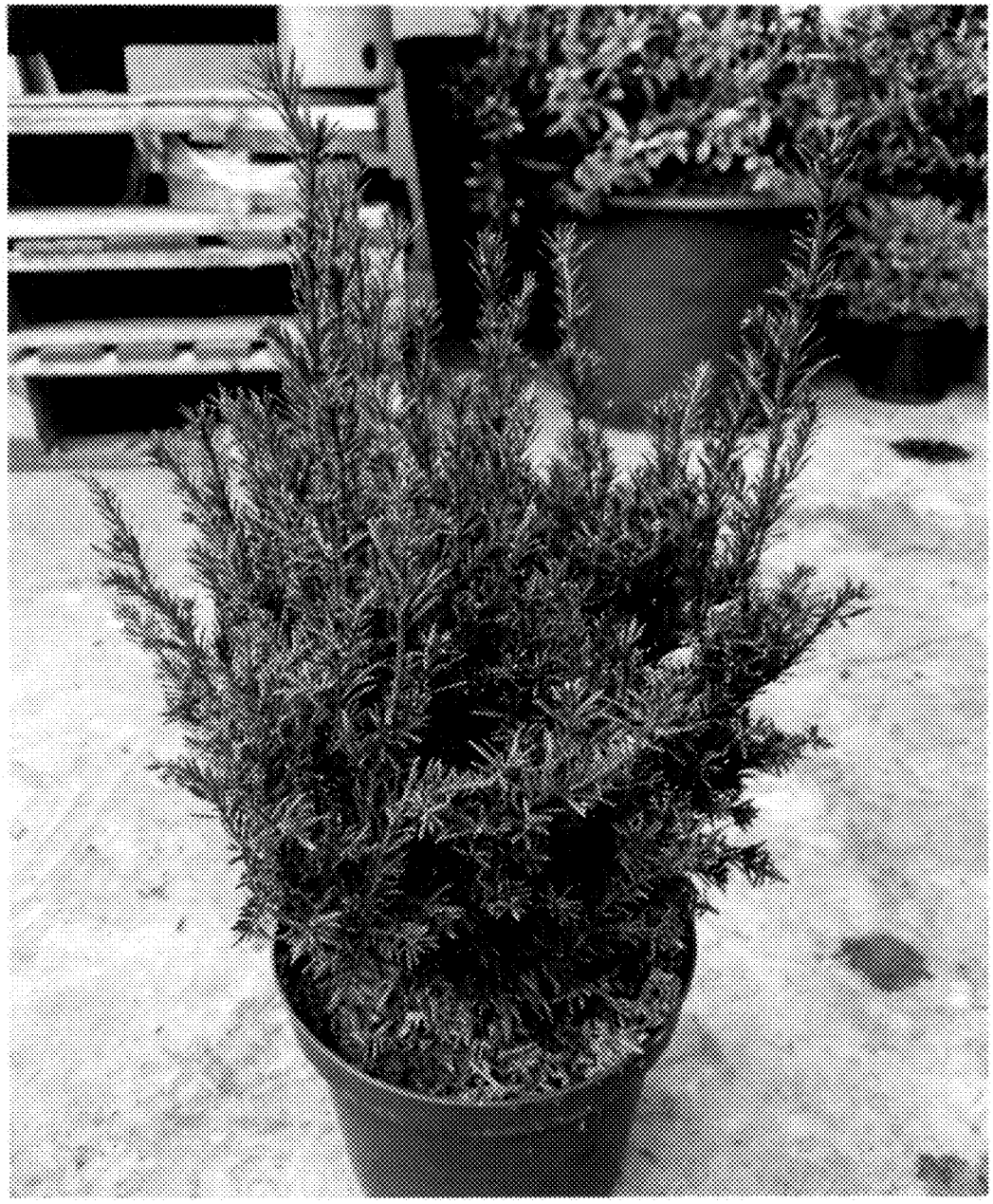
Figure 2:
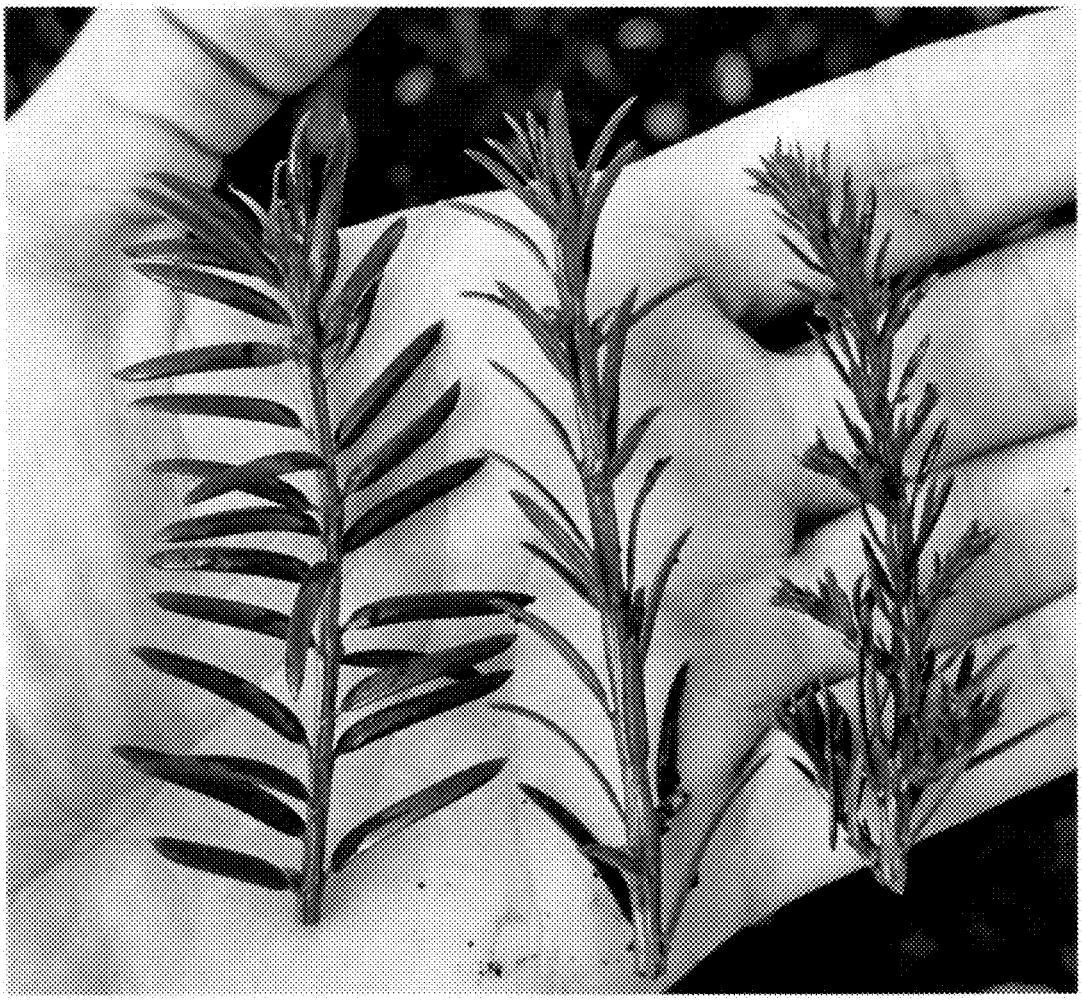

The photograph in FIG. 2 provides a comparison between sprig of an unpatented plant of the species *Taxus baccata* (left), *Taxus* x *media* 'HER2009T01' (middle), and 'HER2016T02' (right).

The colors in the photographs are as close as possible with the photographic and printing technology utilized and the color values cited in the detailed botanical description accurately describe the colors of the new *Taxus*.

DETAILED BOTANICAL DESCRIPTION

The following is a description of 3-year-old plants as grown outdoors in 19-cm containers in Beerse, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen shrub.

*Plant habit*.—Upright, very dense (bushy), and compact.

*Height and spread*.—Average of 33 cm in height, 22 cm in width as a 3-year-old plant grown in a container, and reaches about 40 cm in height and 30 cm in spread as a 4-year-old plant in the landscape.

*Hardiness*.—At least in U.S.D.A. Zones 5 to 7.

*Diseases and pests*.—No resistance or susceptibility to diseases or pests has been observed.

*Root description*.—Fibrous.

*Propagation*.—Stem cuttings.

*Root development*.—4 to 5 months to produce a rooted plug, 1.5 years to produce a fully rooted plant in a 10.5 cm container.

*Growth rate*.—Moderate.

Branch description:

*Branch shape*.—Rounded.

*Branch color*.—New emerging stems; 144A, mature stems; 144A with an overcoat of 199B, bark and older stems; 199A and 199B.

*Branch aspect*.—60° to 80° from horizontal.

*Branch size*.—Main stems; up to 34 cm in length and an average 6 cm in diameter, lateral stems; up to 34 cm in length and an average of 5 mm in diameter.

*Branch strength*.—Strong.

*Branch surface*.—Lateral branches; slightly glossy and smooth, old wood and bark; scaly and matte.

*Branch number*.—An average of 2 main stems and 6 lateral branches.

*Branching habit*.—Well-branched.

*Internode length*.—Average of 1.7 cm.

Foliage description:

*Leaf shape*.—Linear.

*Leaf division*.—Simple.

*Leaf arrangement*.—Alternate, whorled.

*Leaf base*.—Decurrent.

*Leaf aspect*.—Between 30° and 60° to horizontal.

*Leaf apex*.—Acute to acuminate.

*Leaf fragrance*.—None.

*Leaf venation*.—Not distinguishable, mid-vein only visible, upper surface color matches leaf surface, lower surface 137A.

*Leaf margins*.—Entire.

*Leaf attachment*.—Petiolate.

*Leaf surface*.—Upper surface; smooth, slightly glossy, lower surface matte.

*Leaf size*.—Average of 2.2 cm in length and 2 mm in width.

*Leaf quantity*.—Average of 30 on a branch 6 cm in length.

*Leaf color*.—Young upper and lower surface; N144A to N144C, mature upper surface; 139A, mature lower surface 137B to 137C, base 137A.

*Leaf bud*.—3 mm in length, 2 mm in width, N199C, covered with scales 1 mm in length and width, 139A in color.

*Petioles*.—Average of 2 mm in length, 1 mm in width, smooth, slightly glossy surface, strong, both surfaces N199A in color and blend into leaf color at the ends.

Inflorescence description: No flowers have been observed to date.

It is claimed:

1. A new and distinct cultivar of *Taxus* plant named 'HER2016T02' as herein illustrated and described.

* * * * *